(12) United States Patent
Miggantz

(10) Patent No.: US 6,976,842 B1
(45) Date of Patent: Dec. 20, 2005

(54) DEVICE FOR LOCAL SUB-GINGIVAL APPLICATIONS OF DENTAL MEDICATIONS

(76) Inventor: Richard J. Miggantz, 100 Bentley Dr., Pittsburgh, PA (US) 15238

( * ) Notice: Subject to any disclaimer, the term of this patent is extended or adjusted under 35 U.S.C. 154(b) by 70 days.

(21) Appl. No.: 10/194,636

(22) Filed: Jul. 12, 2002

(51) Int. Cl.⁷ .................................................. A61C 9/00
(52) U.S. Cl. ........................................ 433/80; 433/141
(58) Field of Search ............................... 433/80, 82, 87, 433/89, 136, 140, 141, 148, 149

(56) References Cited

U.S. PATENT DOCUMENTS

| | | | |
|---|---|---|---|
| 1,586,302 A * | 5/1926 | Funk |
| 3,742,942 A * | 7/1973 | Westline |
| 4,512,769 A * | 4/1985 | Kozam et al. |
| 4,575,375 A | 3/1986 | Kozam |
| 4,787,845 A | 11/1988 | Valentine |
| 4,846,200 A | 7/1989 | Wiley |
| 4,854,867 A | 8/1989 | Meinershagen |
| 4,930,920 A * | 6/1990 | Fitzig et al. |
| 4,995,403 A | 2/1991 | Beckman et al. |
| 5,002,077 A | 3/1991 | Wiley |
| 5,024,600 A * | 6/1991 | Kline |
| 5,085,585 A | 2/1992 | Zimble |
| 5,100,319 A * | 3/1992 | Baum |
| 5,188,617 A | 2/1993 | Linder |
| 5,244,387 A | 9/1993 | Fuierer |
| 5,507,646 A * | 4/1996 | Roth |
| 6,007,333 A | 12/1999 | Callan et al. |

* cited by examiner

Primary Examiner—Cary E. O'Connor
(74) Attorney, Agent, or Firm—Reed Smith LLP

(57) ABSTRACT

A device for use at least in conjunction with powdered, time-released, periodontal medication, with a view to improving at least upon problems associated with conditional applicators for such medications. Such a device may be in the shape of a hollow, half-cone with a tubular holding element attached to the top of the cone for rotational adjustments. The thin conical shape at the apex of the assisting device penetrates under the gum-line (into the gingival crevice) naturally. The device expands and maintains a sub-gingival space between the gingiva (gum-line) and the tooth. This allows the syringe tip to expulse the medication into the gingival crevice via at least three techniques.

28 Claims, 11 Drawing Sheets

DEVICE FOR LOCAL SUB-GINGIVAL APPLICATIONS OF DENTAL MEDICATIONS

FIELD OF THE INVENTION

The present invention relates generally to dental equipment and, more particularly, to dental implements that are configured for accessing gingival crevices.

BACKGROUND OF THE INVENTION

Periodontal disease and its treatment require an anatomic understanding of an important dental structure (i.e., physiological feature) known as the gingival crevice. This "gingival crevice" can be likened to how a turtleneck sweater fits around a person's neck. If one places a hand between one's neck and the turtleneck sweater, the intervening space could be likened to a gingival crevice. On one side of the hand, the neck could represent the white outer (enamel) surface of a tooth, or even the lower yellow part of the tooth's root surface. On the other side of the hand, the inside collar of the turtleneck sweater could represent the inside lining of the gum tissue surrounding a tooth. Again, the intervening space between the neck and turtleneck sweater would correspond to a gingival crevice.

It is well known that, immediately upon the completion of a dental cleaning, a distinct biological process begins. Saliva in the mouth coats the clean tooth, providing a sticky coating that attaches to the tooth structure. Bacteria in the mouth are then able to attach to the sticky coating and begin multiplying exponentially. During the bacterial lifecycle, the bacteria produce enzymes and toxins that are capable of entering the gingival crevice. Once inside the crevice, the bacteria release these enzymes and toxins which are able to create microscopic ulcers on the inside tissue wall of the gingival crevice. This can result in bleeding inside the gingival crevice, thus eventually allowing the bacteria to enter the microscopic holes created in the tissues of the gingival crevice. Once inside the gum tissue, the bacteria can destroy deeper structures such as connective tissues and blood vessels and could progress even deeper, perhaps eventually reaching and even destroying the bone that holds the teeth in place.

In the past, dental treatment has relied on the use of mechanical instruments to scrape the root and tooth structures that lie inside the gingival crevice in order to control the aforementioned disease process. There have even been attempts in the past to assist in the control of periodontal disease by using liquid or gel medications that are applied by thin metal or plastic syringe tips placed into the gingival crevice. Recently, however, the first "new generation" of time released sub-gingival powdered medications has been released commercially, as of the year 2001 (namely, the "ARESTIN" medication developed by Orapharma, Inc., of Warminster, Pa.). It is recognized that the administration of these and future medications will likely be dependent upon a syringe-like cartridge for application.

A current, conventional syringe tip is 1.5 mm wide on its outside tip diameter and will not easily begin to submerge into the gingival crevice; gingival crevices generally allow for the safe sub-gingival passage of structures that are, at a maximum, ½ mm wide. Another difficulty with this type of syringe/cartridge applicator is that it is rigid and cannot easily be angulated or rotated to reach many areas of the mouth. Therefore, a need has been recognized in connection with assisting in the application of medications to be placed inside the gingival crevice.

It is typical for the cell lining of the gingival crevice to adhere to the tooth's enamel or root surface. Ideally, then, the gingival crevice should be opened at its entry along the gum-line and then penetrated and expanded with deeper progression into the crevice. Maintaining this newly opened space is crucial in order to allow the medication to be applied in proper bulk and dosage. This means that the medication will easily enter the gingival crevice and fill up the potential space created by the assisting device.

Therefore, a need has been recognized in connection with providing an assisting device that may be reliably placed by a dentist. The device should preferably be constructed with enough strength and rigidity to withstand the biological resistances found in the tissue wall making up the gingival crevice. The device should also be readily adaptable to the medication applicator and yet be adjustable for individual patients. The device, also should not cause injury to the gingival crevice and should be comfortable for the patient.

A large need has thus been recognized in connection with providing an optimized, applicator-assisted device for delivering powdered medication.

In the context described hereinabove, the emergence of a time-released powdered medication since 2001 has increased the use of non-surgical treatment for periodontal diseases. Conventional plastic syringe tips used for the application of this (and future) medications is fraught with the following technical and biological problems:

1. The syringe tip is too large to enter the gingival crevice comfortably and safely.
2. The medications are unable to reach the bottom of the crevice in a consistent manner.
3. The syringe tip is unable to carefully maintain an open space in the gingival crevice that is large enough to hold a full dosage of the medication.
4. The application tip of the syringe is not adjustable enough to alter angulations in a way that allows the syringe tip to enter the gingival crevice.
5. The application tip of the syringe is not adjustable at all for rotational movement in a way that allows the syringe tip to enter the gingival crevice.

Needs have thus also been recognized in connection with overcoming the above-listed problems and with providing a medication-assisting device that can be used in conjunction with an application syringe tip (or future applicator tips) of current and future medications.

SUMMARY OF THE INVENTION

It is believed that the items broadly contemplated herein can play a significant role in the future application of medications, time-released powdered or otherwise, that are placed locally into the gingival crevice. The newer time-released medications will most likely continue to be packaged and applied by a cartridge/syringe applicator similar to one mentioned heretofore. Therefore, it is believed that embodiments of the present invention will be well-suited to overcome the existing problems discussed heretofore.

In this vein, broadly contemplated herein is a device for assisting in the placement of sub-gingival, locally placed dental medications. It allows for locating and aligning a medication applicator during the initial entry into the gingival crevice. The assisting device then allows for the complete passage of dental medications into the deeper regions of the gingival crevice. This is followed by the safe removal of the assisting device upon completion of the applied medication.

In summary, there is broadly contemplated, in accordance with at least one presently preferred embodiment of the present invention, instrumentation for assisting in the administration of dental medication, the instrumentation comprising: a forward portion adapted for insertion into a gingival crevice; and a control portion adapted for facilitating maneuverability of the forward portion.

Further, there is broadly contemplated, in accordance with at least one presently preferred embodiment of the present invention, a method of administering dental medication, the method comprising the steps of: providing at least one cartridge adapted to administer medication to a gingival crevice; and providing instrumentation comprising: a forward portion adapted for insertion into a gingival crevice; and a control portion adapted for facilitating maneuverability of the forward portion; the forward portion being adapted to accommodate the at least one cartridge.

BRIEF DESCRIPTION OF THE DRAWINGS

The present invention and its presently preferred embodiments will be better understood by way of reference to the detailed disclosure herebelow and to the accompanying drawings, wherein:

FIG. 1.A is a perspective view of a cone with a plane cutting it in half.

FIG. 1.B is a perspective view of one half of a cone

FIG. 1.C is a perspective view of a half-cone and of parallel cuts to be made.

FIG. 1.D is a perspective view of a completed base of an assisting device.

FIG. 2.A is a perspective view of a unified assisting device formed from a tubular holding element and assisting base.

FIG. 3.A is a perspective view of a solid rod for fitting into a dental handle.

FIG. 3.B is a perspective view of solid rod inserted into a dental handle.

FIG. 3.C is a perspective view of a handle assembly incorporated into an assisting device.

FIG. 4.A is a schematic side view similar to FIG. 4.0 but showing an inventive assisting device.

FIG. 4.B is substantially the same view as FIG. 4.A but additionally illustrating a manner by which an assisting device may open and maintain space in a gingival crevice.

FIG. 4.C is substantially the same view as FIG. 4.B but showing full placement of an assisting device in a gingival crevice.

FIG. 5.A is a schematic side view of an assisting device and medication syringe tip placed in a gingival crevice.

FIG. 6.A is a schematic side view of an assisting device subsequent to rotation of the same towards a tooth while opening an apex of the assisting device.

FIG. 7.A is substantially the same view as FIG. 7.0, but showing lateral and fulcrum movements of an assisting device.

FIG. 7.B is substantially the same view as FIG. 7.0, but showing the simultaneous removal of an assisting device and placement of a syringe tip into a gingival crevice.

FIG. 7.C is substantially the same view as FIG. 7.0, but showing the application of medication into a gingival crevice.

FIG. 8.A is substantially the same view as FIG. 8.0, but showing lateral and fulcrum movements of an assisting device.

FIG. 8.B is substantially the same view as FIG. 8.0, but showing syringe tip placement into a crevice.

FIG. 8.C is a side schematic view of an assisting device and syringe tip inside a gingival crevice.

FIG. 8.D is substantially the same view as FIG. 8.C, but showing a syringe tip inside a gingival crevice.

DESCRIPTION OF THE PREFERRED EMBODIMENTS

Figure 1:
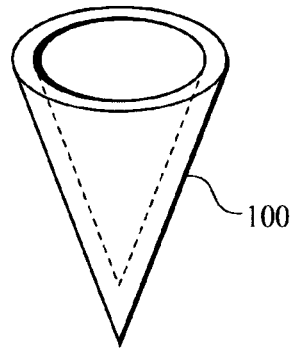
FIG. 1.0 is a perspective view of a hollow cone.
Figure 1A:
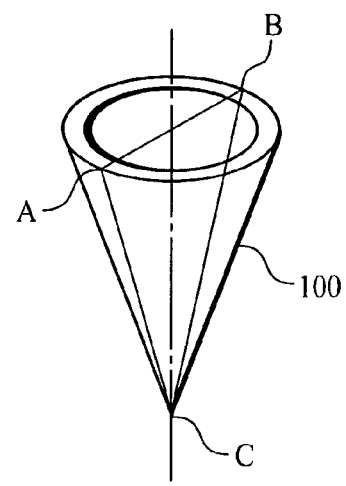
Figure 1B:
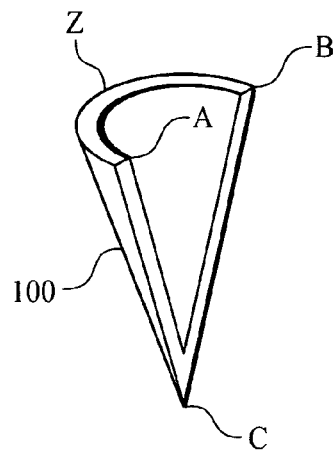
Figure 1C:
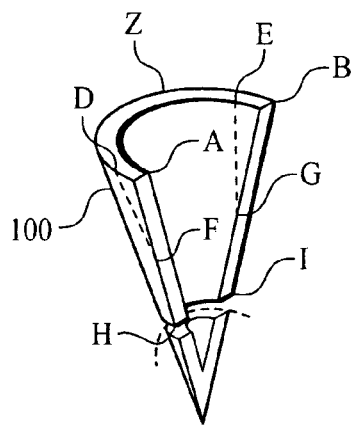
Figure 1D:
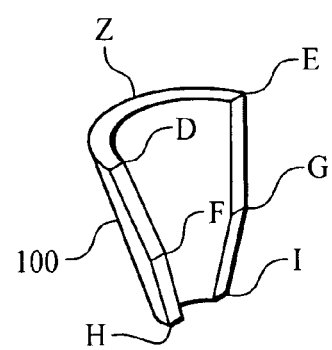

With reference to FIGS. 1.A–1.D, an assisting device in accordance with at least one embodiment of the present invention can best be visualized by starting with the structure of a hollow geometric cone 100. If such a cone 100 is then cut in half from top to bottom as seen in FIGS. 1.A and 1.B, and then further cuts are made as shown in FIGS. 1.C and 1.D, then a minimum diameter or radius of the modified structure 100 will be towards what was the apex of the cone. Preferably, the larger semi-circular portion at the top of the modified cone structure 100 will have a point Z that will serve as a locus of connection to a hollow tubular structure. The lowermost portion of the modified cone structure 100, as shown in FIG. 1.D will preferably be thin enough and small enough to enter the 0.5 mm (or so) natural opening of a human gingival crevice. The problem 1 discussed previously is thus solved.

Figure 2:
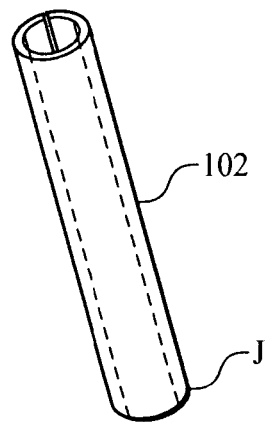
FIG. 2.0 is a perspective view of a hollow tubular structure for making up the holding element of the base of an assisting device.
Figure 2A:
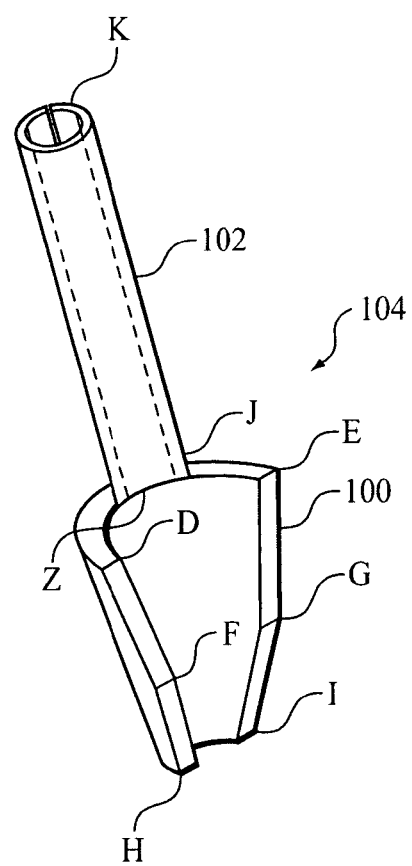

On the other hand, a hollow tubular structure 102, as shown in FIG. 2.0, will preferably serve as a holding element for the basic body (100) of an assisting device having the previously described "modified cone" shape, with the result being a unified structure 104 as shown in FIG. 2.A. This will further permit rotation of the assisting device 100, thereby achieving easier entry into the gingival crevice at any position of the mouth. This thus solves problems 4 and 5 discussed previously.

Once the assisting device 104 enters a gingival crevice it will preferably serve to penetrate, expand and maintain the newly opened space. This thus solves problem 3 discussed previously.

Once inside a gingival crevice, assisting device 104 will preferably be operable via any conceivably suitable technique (three of which are explained herebelow) for applying medication to a fully opened gingival crevice. This solves problem 2 discussed previously.

Figure 4:
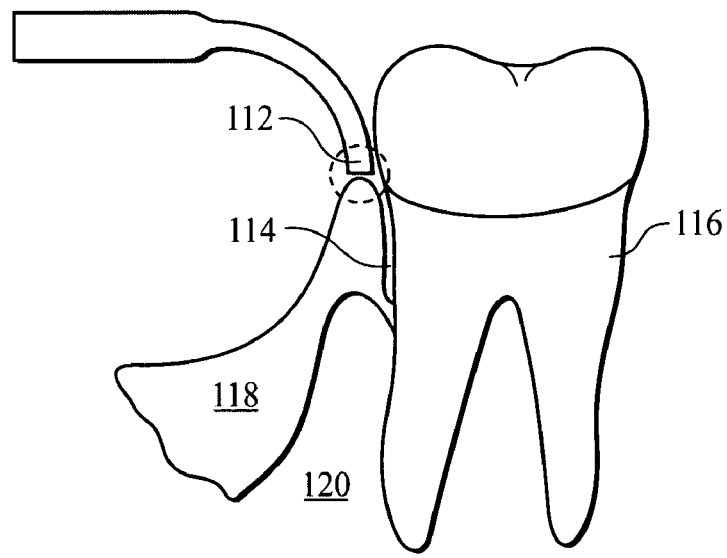
FIG. 4.0 is a schematic side view which relates the size of a conventional medication applicator syringe tip to a gingival crevice.
Figure 4A:
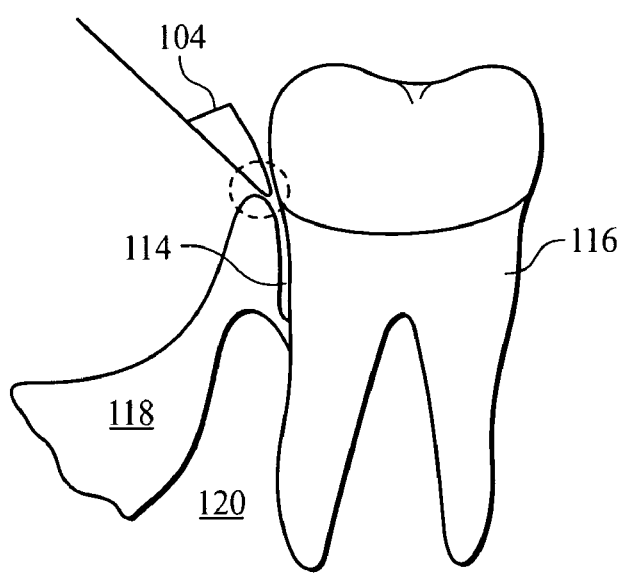
Figure 4B:
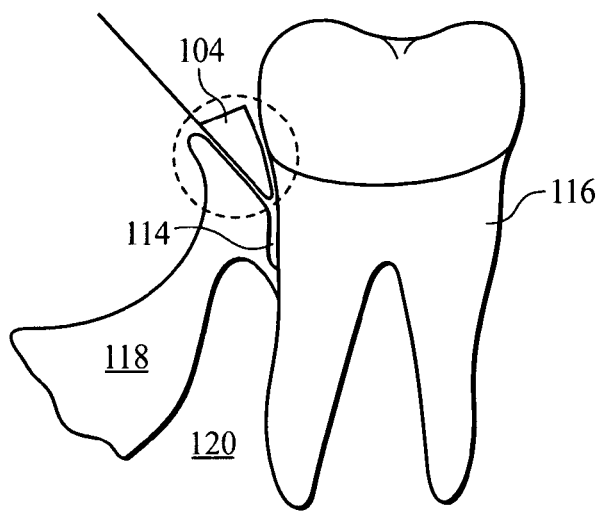
Figure 4C:
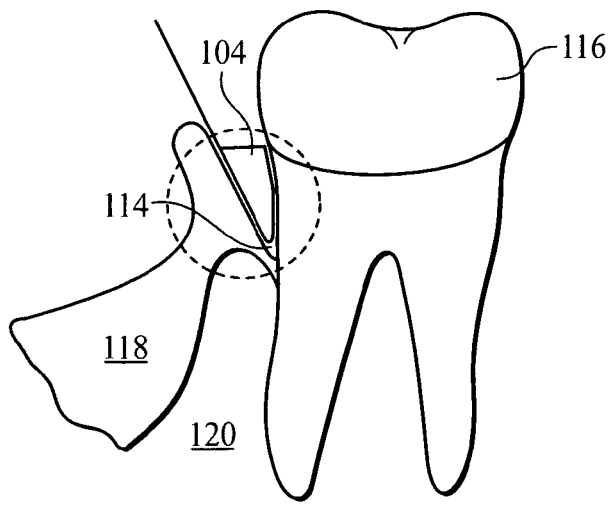

In a "leveraged opening" technique, as illustrated in FIGS. 4.A–6.A, that portion of the assisting device 104 that is concave preferably faces the tooth as it enters the gingival crevice. This can be seen clearly in FIGS. 5.0 and 5.A. As shown there, obtuse angle DFH forms a fulcrum at point F. This fulcrum permits the assisting device 104 to be pushed as a lever toward the tooth via the hollow tubular holding portion of the assisting device. In turn, the apex of the assisting device 104 is preferably moved in an opposite direction away from the root of the tooth, as seen in FIGS. 6.0 and 6.A. The rotational movement around the fulcrum points F and G allows the medication syringe tip to enter further past and reaching near the end of the assisting device, FIG. 6.A. This allows a syringe tip to apply the medication past the assisting device and into the opened apex of the gingival crevice.

In a "shoehorn technique" (see FIGS. 7.0–7.C), the assisting device 104 is made to slide easily into a gingival crevice and travel to the bottom of the crevice. The assisting device 104 is again preferably rocked back and forth at the fulcrum Points, F and G, stretching the gingival crevice away from the tooth and root. The assisting device 104 is then preferably removed from the crevice until only about 20% of the device remains in the crevice. At this point, the syringe tip applicator slides easily between the assisting device and the tooth, carefully entering the crevice. Once the syringe tip is about 1.5 mm inside the crevice it is possible to remove the assisting device. The syringe tip is now free to penetrate further into the gingival crevice and to apply the medication.

In a "time retraction" technique, the assisting device 104 is preferably placed fully into a gingival crevice. The device 104 is then preferably allowed to remain in the gingival crevice for 15 to 20 seconds while rocking the device periodically at the fulcrum Points F and G. This will stretch the inner walls of the gingival crevice away from the tooth. At the appropriate time, the assisting device is removed and the syringe tip applicator is placed into the space created by the assisting device. The syringe tip applicator can now penetrate further and the medication can be applied.

The disclosure now turns to a more detailed discussion of the functioning of an assisting device and handle assembly as a unified, functional unit and of the three prior discussed techniques for applying medications into local sites of the sub-gingival crevice that lie around teeth.

FIG. 1.0 shows a cone 100 upright with its wide mouth facing up and the sharp apex facing downward.

As shown in FIG 1.A, by utilizing the plane ABC, one can visualize where the cone will be cut in half from top to bottom.

FIG. 1.B shows the results of cutting the cone 100 in half from top to bottom. An additional point Z is shown as the mid-point of the remaining top of the cone.

FIG. 1.C shows additional points placed on the cone. A single cut will preferably be made at line D-F, which will parallel the cut made at line E-G. The purpose of this cut is to create two obtuse angles, angle DFH, and angle EGI. These angles will act as a fulcrum against the tooth structure that they contact via. points F and G. An additional cut is preferably made beneath arc H-I, eliminating the apex of the cone entirely.

FIG. 1.D shows the final result of the alterations discussed above.

FIG. 2.0 shows a hollowed out cylindrical tube 102 that is oriented vertically. The top part of the cylindrical tube is marked as point K. The bottom part of the cylindrical tube is marked as point J.

FIG. 2.A shows the manner by which point J of the vertically oriented cylindrical tube 102 preferably attaches to point Z of the basic body of the assisting device 100. The hollow tube 102 and basic body 100 make up a unified structure that can be referred to as the "assisting device" 104.

Figure 3:
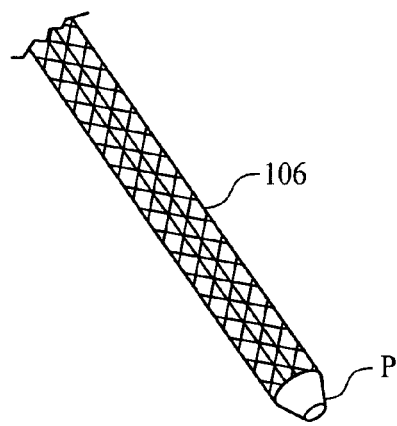
FIG. 3.0 is a perspective view of a conventional hollow dental instrument handle.
Figure 3A:
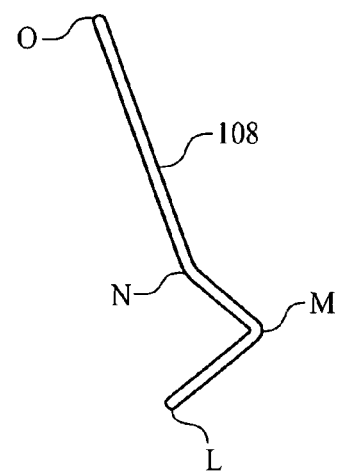
Figure 3B:
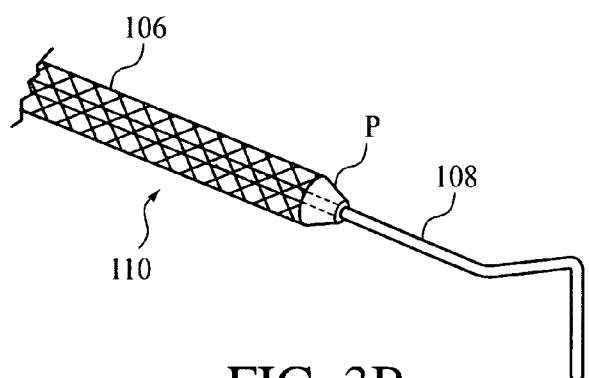
Figure 3C:
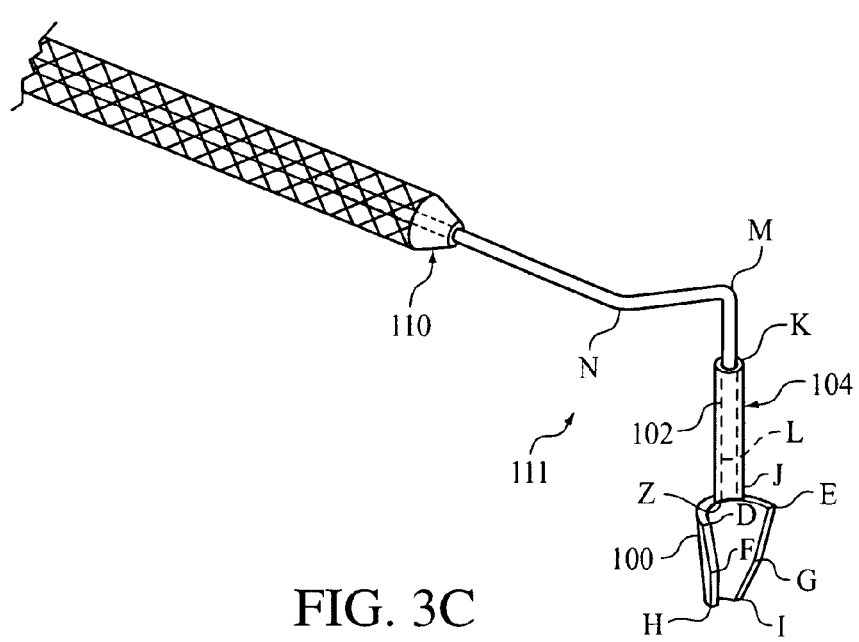

FIG. 3.0 shows a conventional dental instrument handle, which may preferably be used here as a finger-grip.

FIG. 3.A shows a cylindrical solid rod 108 having two separate angles, acute angle LMN and obtuse angle MNO. The cylindrical solid rod 108 also presents two attachment ends referred as point O and point L.

FIG. 3.B. shows point O of the cylindrical solid rod 108 connecting into point P of the hollow dental instrument handle 106. The connection of these two pieces is preferably through a press fit that is non-movable and non-rotational. Once joined, these two pieces can be referred to as the "handle assembly," 110.

FIG. 3.C. shows how the handle assembly 110 and the assisting device 104 are preferably pressure fit together. This pressure fit at point L of the cylindrical solid rod to point K of the hollowed tube, however, allow for manual rotation between the handle assembly, and the assisting device 104. The unified structure will henceforth be indicated at 111.

FIG. 4.O. shows how a conventional medication applicator syringe-tip (112) will not fit passively into the gingival crevice 114. The syringe tip here (112) is 1.5 mm wide, while the crevice 114, as well-known, will typically only accept objects with a maximum width of 0.5 mm. Also shown, for a better understanding of this and other concepts, are tooth 116, gums 118 and bone 120.

In accordance with a "leveraged opening technique", FIG. 4.A. shows the assisting device 104 entering the gingival crevice 114 at an angle that allows parallel surfaces F-H and G-I (see FIG. 1.D), to contact the tooth structure (116) and begin sliding into the crevice 114. The width of the tip on the assisting device 104 may preferably be around 0.5 mm, thus allowing gentle hand pressure to guide the device 104 easily into the crevice 114. This begins the process of separating the internal wall of the gingival crevice 114 from the root, or enamel surface, of tooth 116. It is recognized that patients find this easy to tolerate without local anesthesia.

FIG. 4.B. shows the continued separation of the gingival crevice 114 as the assisting device 104 penetrates halfway into the crevice 114. The separation is maintained due to the gradual widening of the conical assisting device 104.

FIG. 4.C. shows the full penetration of the assisting device 104 into the gingival crevice 114 while maintaining separation of the inner surface of the crevice from the tooth 116.

Figure 5:
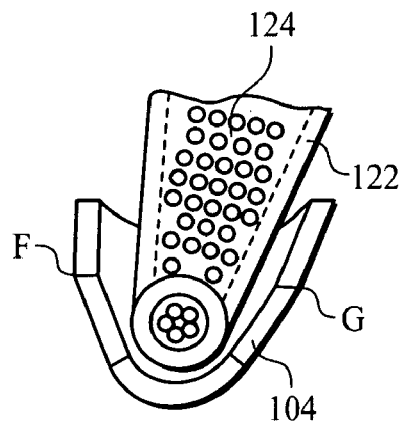
FIG. 5.0 is a bottom view of an assisting device with a medication syringe tip in place.
Figure 5A:
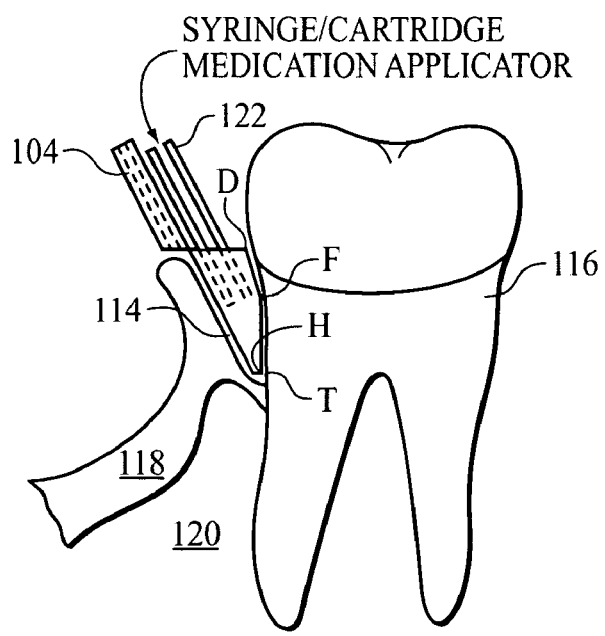
Figure 6:
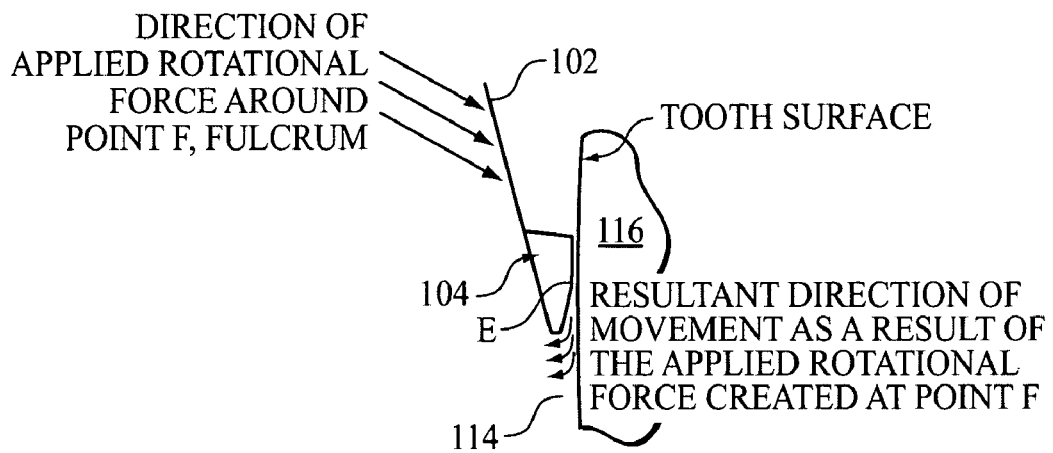
FIG. 6.0 is a side view of an assisting device illustrating a rotational fulcrum.
Figure 6A:
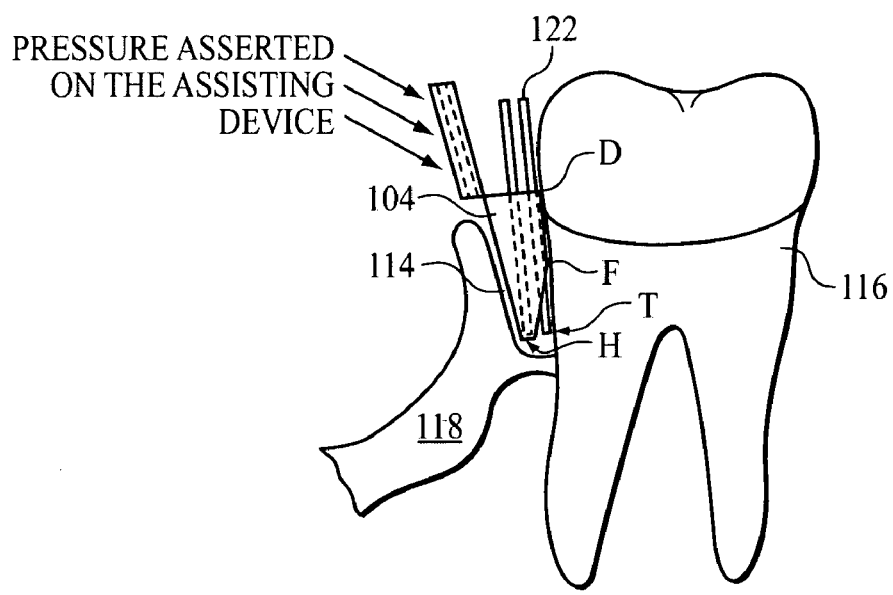

FIG. 5.O. shows how the assisting device and a medication syringe tip 122 (containing powdered medication 124) appear when viewed from the vantage point of the root of the tooth. Points F and G represent the fulcrum of the assisting device 104 as it rests against the root of the tooth. A preferred 0.5 mm internal diameter of the syringe 122 is seen as it relates to the preferred circular shape of the assisting device tip. Once full penetration of the assisting device 104 into the crevice has occurred, the rocking of the fulcrum will open up (0.5 mm.), thus providing enough space for the medication to be expelled into the gingival crevice.

FIG. 5.A. shows the full penetration of the assisting device 104 into the crevice 114. Point H is the most apical (i.e., bottom) portion of the assisting device 104 and rests against the root of the tooth at point T. (Though a slight separation is shown between points H and T in the drawing, this is merely for illustrative purposes; it should be understood that essentially no such separation is preferably involved.) Due to this tight juncture, it will essentially be impossible at this stage to release the medication 124 from the syringe tip 122 into the crevice. During this time, though, the assisting device 104 continues to maintain the separation of the inner surface of the crevice 114 from the root surface of the tooth 116. The medication syringe tip 122 can be seen in place between the assisting device 104 and the root of the tooth 116. Preferably, the syringe tip 122 will only be able to penetrate about halfway into the assisting device 104 at this moment.

FIG. 6.O. schematically shows a side view of the assisting device 104 as it rests next to the root of the tooth 116 during full penetration into the gingival crevice 114. Shown is the manner in which the dental handle assembly 110 (see FIG. 3.C.) can apply a force on the hollowed-out cylindrical tube 102 that makes up the superior portion of the assisting device 104. The force from the dental handle allows the assisting device 104 to rock at a fulcrum formed by point F. The resultant action is to create a greater force (due to leverage) at the bottom of the assisting device 104. The force at the bottom of the assisting device tip is in the opposite direction as the force applied to the superior portion of the assisting device 104. This opposite force pressures the bottom of the gingival crevice 114 away from the tooth, allowing the medication syringe tip 122 (see FIG. 5.A) to slide deeper into the crevice and to consummately open a wider space between the assisting device 104 and the root surface of the tooth 116. This allows for complete expulsion of the medication inside the syringe tip (see FIG. 5.A) into the gingival crevice 114. The medication is thence compelled to migrate to the deepest portion of the crevice 114.

FIG. 6.A. shows the assisting device 104 completely penetrating into the gingival crevice 114. The dental handle or handle assembly (not shown) has placed an apical and rotational force on the upper portion of the assisting device 104. This has caused pivoting about Fulcrum F of line F-D, toward the root of the tooth 116. As a consequence of this pivotal movement about point F, the space between points H and T has increased. A change has thus occurred from essentially no opening (as seen in FIG. 5.A), to about a 1.5 mm opening here. The expansion of this space between points H and T thus allows the syringe tip 122 to freely release the medication into the bottom of the gingival crevice 114.

Figure 7:
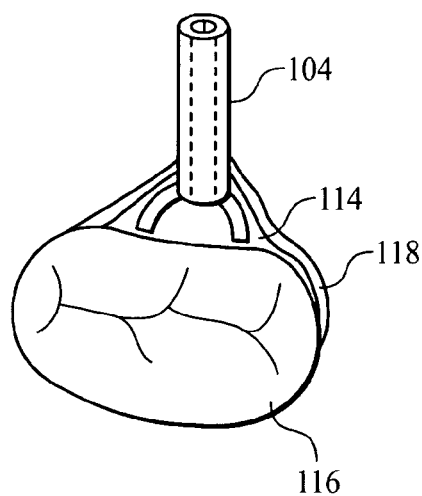
FIG. 7.0 is a top schematic view showing the base of an assisting device in place.
Figure 7A:
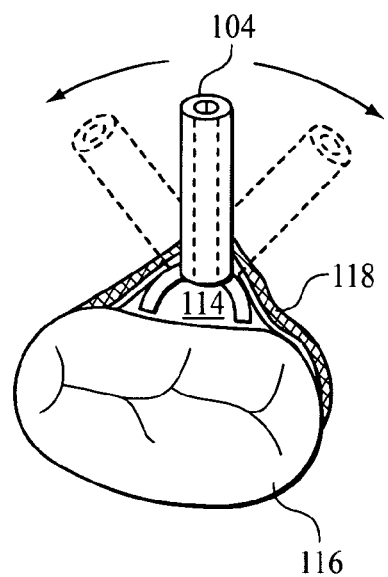
Figure 7B:
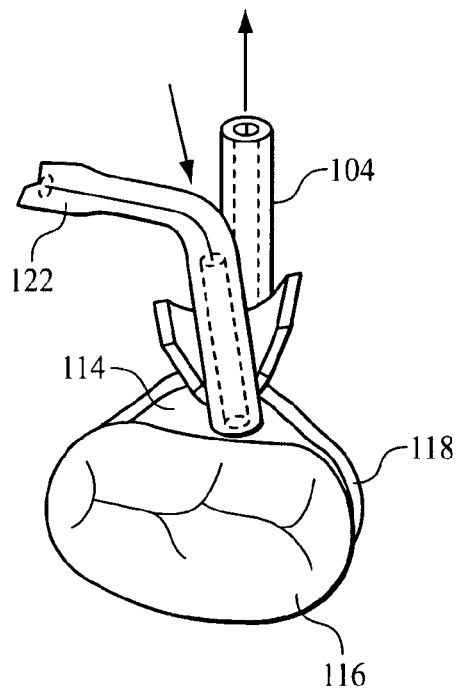
Figure 7C:
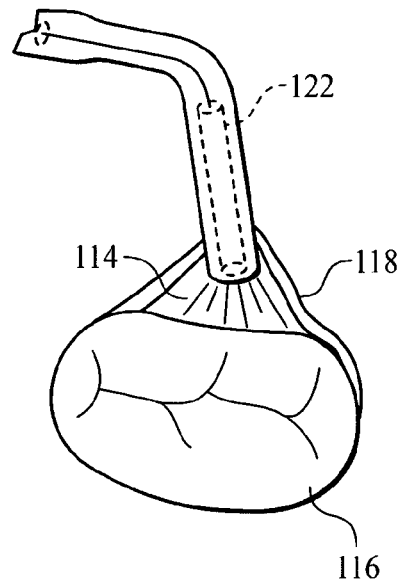

In accordance with a "shoehorn technique", FIG. 7.O. first shows assisting device 104 in place with gingival crevice 114 open. Also shown are tooth 116 and gums 118.

FIG. 7.A. illustrates a lateral and forward rocking motion of assisting device 104 to stretch the gingival crevice 114.

FIG. 7.B. shows the assisting device 104 pulled out of the crevice 116 until only about 20% of it actually remains inside the crevice 114. At this point in time the medication syringe 122 is preferably placed into the crevice 114 while in contact with the assisting device 104. Once syringe tip 122 is inside crevice 114, the assisting device is pulled out.

FIG. 7.C. shows the medication syringe tip 122 placing the medication into the crevice 114. Preferably, medication will be expelled by positive pressure on a plunger attached to the syringe tip 122.

Figure 8:
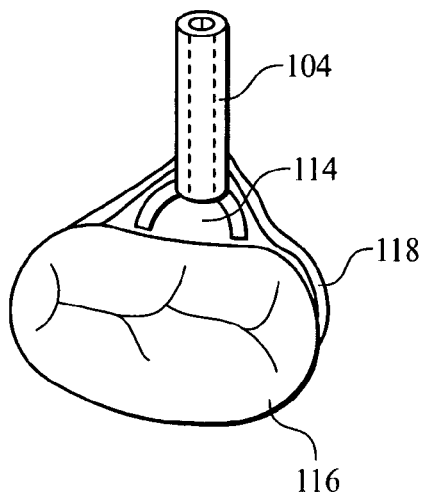
FIG. 8.0 is a top schematic view of an assisting device in a crevice.
Figure 8A:
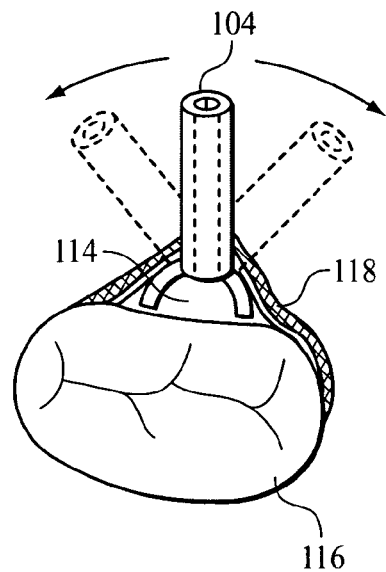
Figure 8B:
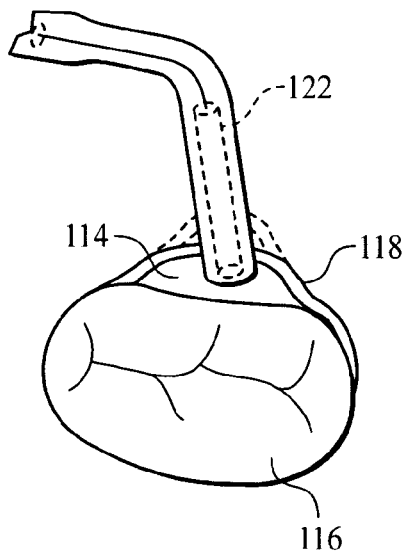
Figure 8C:
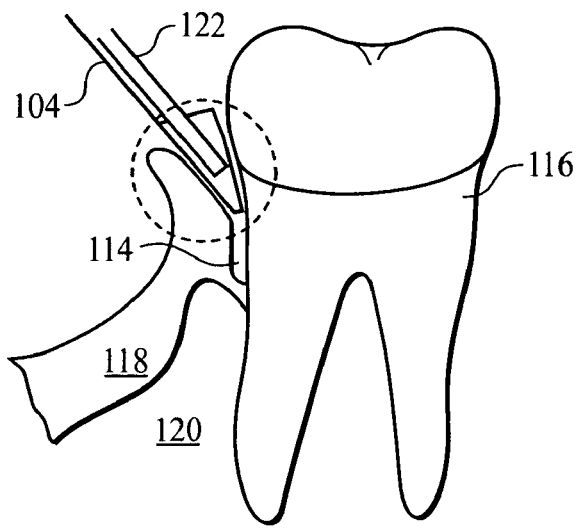
Figure 8D:
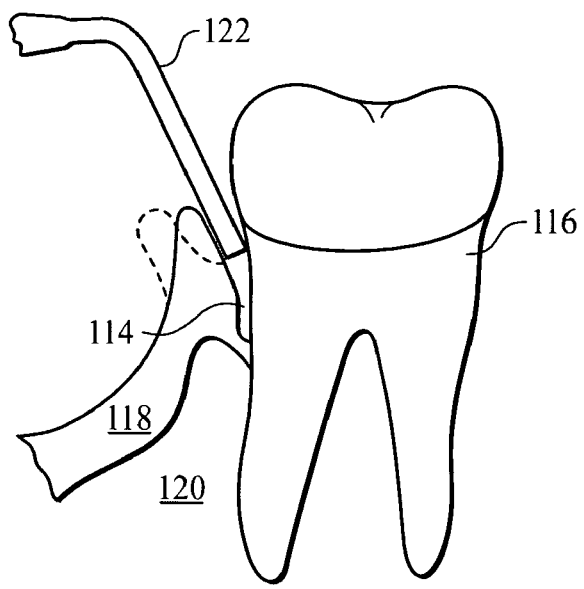
Figure 9A:
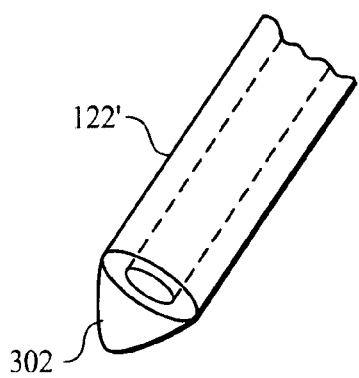
FIGS. 9.A through 9.E show, in perspective view, various ends and end portions that can be utilized in connection with, or associated with, syringe tips.
Figure 9B:
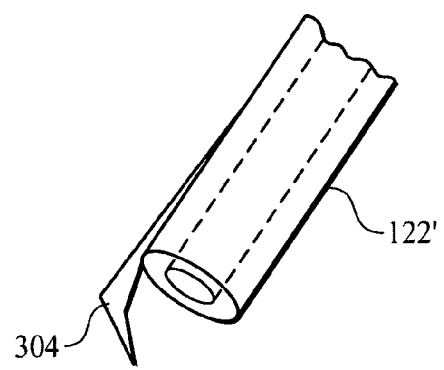
Figure 9C:
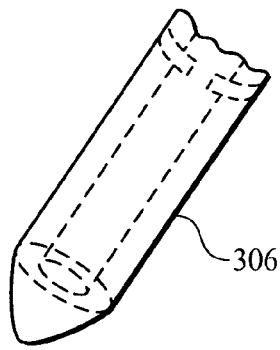
Figure 9D:
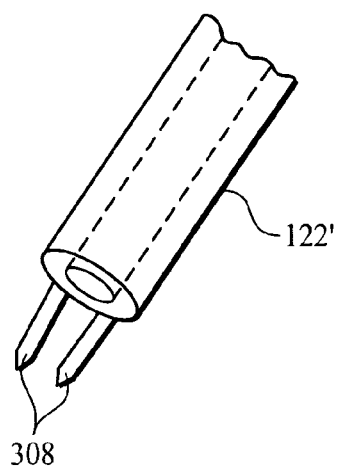
Figure 9E:
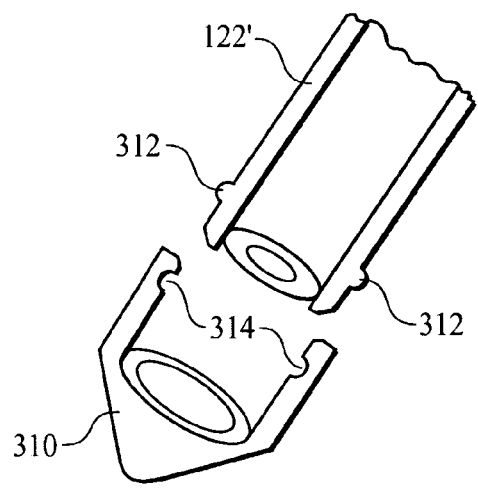

In accordance with a "timed retraction technique", FIG. 8.0. first shows the assisting device 104 in place, as in FIG. 7.0.

FIG. 8.A. shows lateral and forward rocking of the assisting device 104 in the crevice 114. This is preferably followed by a 15–20 second holding period of the device 104 in place, so as to stretch a gingival crevice entry area.

FIG. 8.B. shows the space that may be left open by the 15–20 second holding of the device 104 in place. The medication syringe tip 122 can now easily enter the gingival crevice 114 and proceed to the base of the crevice 114 for the administration of the medication.

FIG. 8.C. shows a side view of the assisting device 104 (with syringe top 122) opening the gingival crevice 114.

FIG. 8.D. shows the medication syringe 122 easily entering the gingival crevice 114 and passing further into the crevice to administer medication.

In both FIGS. 8.B. and 8.D., dotted lines show the maximum expansion of the gums 118 defining gingival crevice 114 before they start to relapse towards a "normal" position. The solid lines depicting gums 118 thus illustrate that there is still a sufficient opening for syringe tip 122 to be placed into crevice 114.

Though particular embodiments of various components have been described hereinabove, it should be understood that a large variety of similar components, performing similar functions, are also broadly contemplated in accordance with the present invention. For instance, standard syringe tips, which are generally hollow and generally present no particular structural embellishments at the exit portion where medication is expelled, are generally contemplated in accordance with the embodiments of the present invention. However, a wide range of other possible syringe tips is broadly contemplated herein, or even other types of "ends" or "end portions" for delivering medication into a gingival crevice and even for providing functions similar to an assisting device as described heretofore.

FIGS. 9.A. through 9.E. show, in illustrative and non-restrictive fashion, different "ends" or "end portions" for delivering medication into a gingival crevice. For example, FIG. 9.A. shows a simple projection 302 integral with a syringe tip 122'.

FIG. 9.B. shows a single projection 304 on a syringe tip 122'. The projection 304 could be attached in essentially any suitable manner to syringe tip 122' (e.g., via a snap-on connection), or could even be integral with it.

FIG. 9.C shows an end portion 306 that can be freely attachable to a syringe tip, e.g. via a clamp-on connection, a screw connection, glue connection, friction fit, etc.

FIG. 9.D. shows a double projection 308 on a syringe tip 122'. The projection 308 could be attached in essentially any suitable manner to syringe tip 122' (e.g., via a snap-on connection), or could even be integral with it.

FIG. 9.E. shows an end portion 310 that can be freely attachable to a syringe tip 122' via a snap-on connection. To this end, syringe tip 122' may include a suitable annular protrusion 312 or the like for being accommodated in a corresponding groove 314 or the like on end portion 310.

It should be appreciated that the arrangements shown in FIGS. 9.A. through 9.E. are but representative of a wide variety of types of solitary instrumentation or add-on instrumentation that could be utilized for facilitating the delivery of medication to a gingival crevice and/or to "mimic" the functions of an assisting device as described heretofore (e.g., to assist in teasing open, retracting, prying or gaining entry into a gingival crevice). Thus, arrangements such as those shown in FIGS. 9.A through 9.E could be used in conjunction with or instead of an assisting device as described heretofore.

If not otherwise stated herein, it may be assumed that all components and/or processes described heretofore may, if appropriate, be considered to be interchangeable with similar components and/or processes disclosed elsewhere in the specification, unless an express indication is made to the contrary.

If not otherwise stated herein, any and all patents, patent publications, articles and other printed publications discussed or mentioned herein are hereby incorporated by reference as if set forth in their entirety herein.

It should be appreciated that the apparatus and method of the present invention may be configured and conducted as appropriate for any context at hand. The embodiments described above are to be considered in all respects only as illustrative and not restrictive. All changes which come within the meaning and range of equivalency of the claims are to be embraced within their scope.

What is claimed is:

1. Instrumentation for assisting in the administration of dental medication, said instrumentation comprising:
   a forward portion;
   said forward portion comprising a tapered portion for insertion into a gingival crevice, said tapered portion being adapted to stretch a gingival crevice to facilitate accommodation in a gingival crevice of a cartridge for administering medication into the gingival crevice; and
   a control portion adapted for facilitating maneuverability of said forward portion;
   said forward portion further including an upper portion integral with said tapered portion, said upper portion generally having a greater width than said tapered portion;
   said tapered portion having an uppermost region and an apical region;
   said tapered portion tapering in size between said uppermost region of said tapered portion and said apical region of said tapered portion;
   said tapered portion of said forward portion being shaped as a truncated half-cone.

2. The instrumentation according to claim 1, wherein:
   said upper portion is formed from a half-cone and includes an uppermost region, having a maximal cross-sectional cone radius, and a lowermost region, having a minimal cross-sectional cone radius;
   said uppermost region of said tapered portion being integral with said lowermost region of said upper portion.

3. The instrumentation according to claim 2, wherein, between said uppermost region of said upper portion and said lowermost region of said upper portion, the cross-section of said upper portion is defined as a partial cone cut at a variable secant, wherein the secant, as a proportion of the cross-sectional cone radius, is minimal at said uppermost region and maximal at said lowermost region.

4. The instrumentation according to claim 3, wherein, at said lowermost region of said upper portion, the variable secant is substantially equivalent to the cross-sectional cone diameter.

5. A method of administering dental medication, said method comprising the steps of:
   providing at least one cartridge adapted to administer medication to a gingival crevice; and
   providing instrumentation comprising:
      a forward portion; and
      a control portion adapted for facilitating maneuverability of said forward portion;
      said forward portion comprising a tapered portion for insertion into a gingival crevice, said tapered portion being adapted to stretch a gingival crevice to facilitate accommodation in a gingival crevice of a cartridge for administering medication into the gingival crevice;
   inserting said tapered portion of said forward portion into a gingival crevice;
   accommodating at least one said cartridge at said forward portion; and
   displacing said forward portion to create a pocket at the gingival crevice and dispensing medication via said at least one cartridge into the pocket created at the gingival crevice.

6. The method according to claim 5, wherein said control portion is fixedly attached to said forward portion.

7. The method according to claim 5, wherein said control portion is adapted for integration with a portion of a dental handle.

8. The method according to claim 7, wherein said control portion comprises a hollowed-out cylindrical portion adapted to receive a portion of a dental handle.

9. The method according to claim 8, further comprising the step of inserting a dental handle in said hollowed-out cylindrical portion of said control portion of said instrument.

10. The method according to claim 5, wherein said displacing step comprises pivoting said forward portion of said instrument about a fulcrum on said forward portion of said instrument.

11. The method according to claim 5, whereby the administration of powdered medication is facilitated.

12. A method of administering dental medication, said method comprising the steps of:
   providing at least one cartridge adapted to administer medication to a gingival crevice; and
   providing instrumentation comprising:
      a forward portion; and
      a control portion adapted for facilitating maneuverability of said forward portion;
      said forward portion comprising a tapered portion for insertion into a gingival crevice, said tapered portion being adapted to stretch a gingival crevice to facilitate accommodation in a gingival crevice of a cartridge for administering medication into the gingival crevice;
   inserting said tapered portion of said forward portion into a gingival crevice and opening the gingival crevice;
   accommodating at least one said cartridge at said forward portion;
   removing said forward portion away from the gingival crevice while leaving said at least one cartridge inserted in the gingival crevice; and
   permitting the egress of medication from said at least one cartridge into the gingival crevice.

13. The method according to claim 12, wherein said control portion is operatively separable from said forward portion.

14. The method according to claim 12, wherein said step of opening the gingival crevice comprises rocking said forward portion of said instrument sufficiently to open the gingival crevice.

15. The method according to claim 12, wherein said step of accommodating said at least one cartridge is performed substantially immediately after opening the gingival crevice.

16. The method according to claim 12, wherein said step of accommodating said at least one cartridge is performed after a predetermined time interval subsequent to opening the gingival crevice.

17. The method according to claim 16, wherein the predetermined time interval is between about 15 seconds and about 20 seconds.

18. The method according to claim 12, wherein said at least one cartridge is adapted to administer powdered medication to a gingival crevice.

19. Instrumentation for assisting in the administration of dental medication, said instrumentation comprising:
   a forward portion;

said forward portion comprising a tapered portion for insertion into a gingival crevice, said tapered portion being adapted to stretch a gingival crevice to facilitate accommodation in a gingival crevice of a cartridge for administering medication into the gingival crevice; and a control portion adapted for facilitating maneuverability of said forward portion;

said forward portion further including an upper portion integral with said tapered portion, said upper portion generally having a greater width than said tapered portion;

said tapered portion of said forward portion being shaped as a truncated partial cone.

20. The instrumentation according to claim 19, wherein said control portion is operatively separable from said forward portion.

21. The instrumentation according to claim 19, further comprising a cartridge adapted to administer medication to a gingival crevice, wherein said forward portion is associated with said cartridge, wherein said forward portion and said cartridge are adapted for selective attachment and detachment with respect to one another.

22. The instrumentation according to claim 19, wherein said control portion is adapted for attachment to a portion of a dental handle.

23. The instrumentation according to claim 22, wherein said control portion comprises a hollowed-out cylindrical portion adapted to receive a portion of a dental handle.

24. The instrumentation according to claim 19, whereby the administration of powdered medication is facilitated.

25. Instrumentation for assisting in the administration of dental medication, said instrumentation comprising:

a forward portion adapted for insertion into a gingival crevice; and a control portion adapted for facilitating maneuverability of said forward portion;

said forward portion including a tapered portion adapted for insertion into a gingival crevice;

said forward portion further including an upper portion integral with said tapered portion, said upper portion generally having a greater width than said tapered portion;

said tapered portion having an uppermost region and an apical region;

said tapered portion tapering in size between said uppermost region of said tapered portion and said apical region of said tapered portion; and said tapered portion of said forward portion being shaped as a truncated half-cone.

26. A method of administering dental medication, said method comprising the steps of:

providing at least one cartridge adapted to administer medication to a gingival crevice;

providing instrumentation comprising:

a forward portion, said forward portion including a tapered portion adapted for insertion into a gingival crevice; and a control portion adapted for facilitating maneuverability of said forward portion;

said forward portion being adapted to accommodate said at least one cartridge;

accommodating at least one said cartridge at said forward portion of said instrument;

inserting said tapered portion of said forward portion into a gingival crevice; and displacing said forward portion to permit the egress of medication from said at least one cartridge into the gingival crevice;

said displacing step comprising pivoting said forward portion about a fulcrum on said forward portion.

27. A method of administering dental medication, said method comprising the steps of:

providing at least one cartridge adapted to administer medication to a gingival crevice; and providing instrumentation comprising:

a forward portion; and a control portion adapted for facilitating maneuverability of said forward portion;

said forward portion comprising a tapered portion for insertion into a gingival crevice, said tapered portion being adapted to stretch a gingival crevice to facilitate accommodation in a gingival crevice of a cartridge for administering medication into the gingival crevice;

inserting said tapered portion of said forward portion into a gingival crevice;

accommodating at least one said cartridge at said forward portion; and displacing said forward portion to facilitate the egress of medication from said at least one cartridge into the gingival crevice;

wherein said displacing step comprises pivoting said forward portion of said instrument about a fulcrum on said forward portion of said instrument.

28. A method of administering dental medication, said method comprising the steps of:

providing at least one cartridge adapted to administer medication to a gingival crevice; and providing instrumentation comprising:

a forward portion; and a control portion adapted for facilitating maneuverability of said forward portion;

said forward portion comprising a tapered portion for insertion into a gingival crevice, said tapered portion being adapted to stretch a gingival crevice to facilitate accommodation in a gingival crevice of a cartridge for administering medication into the gingival crevice;

inserting said tapered portion of said forward portion into a gingival crevice;

accommodating at least one said cartridge at said forward portion; and displacing said forward portion to facilitate the egress of medication from said at least one cartridge into the gingival crevice;

said control portion being adapted for integration with a portion of a dental handle;

said control portion comprising a hollowed-out cylindrical portion adapted to receive a portion of a dental handle; and said method further comprising the step of inserting a dental handle in said hollowed-out cylindrical portion of said control portion of said instrument.

* * * * *